US012658299B2

(12) United States Patent
Banerjee et al.

(10) Patent No.: US 12,658,299 B2
(45) Date of Patent: Jun. 16, 2026

(54) INTELLIGENT SYSTEM FOR AUTOMATICALLY TESTING AND SELECTING FROM MULTIPLE DATA MODELS FOR ACCURATE DIVERSION PREDICTION

(71) Applicant: CERNER INNOVATION, INC., Kansas City, KS (US)

(72) Inventors: Rajdeep Banerjee, Bangalore (IN); Karthik Nagaraja, Bangalore (IN); Wasimakram Binnal, Bangalore (IN); Pradeep Premakumar, Bangalore (IN)

(73) Assignee: CERNER INNOVATION, INC., Kansas City, MO (US)

( * ) Notice: Subject to any disclaimer, the term of this patent is extended or adjusted under 35 U.S.C. 154(b) by 350 days.

(21) Appl. No.: 17/471,752

(22) Filed: Sep. 10, 2021

(65) Prior Publication Data

US 2023/0077660 A1 Mar. 16, 2023

(51) Int. Cl.
| | |
|---|---|
| *G16H 20/10* | (2018.01) |
| *G06F 18/211* | (2023.01) |
| *G06F 18/214* | (2023.01) |
| *G06N 7/01* | (2023.01) |

(Continued)

(52) U.S. Cl.
CPC ........... *G16H 20/10* (2018.01); *G06F 18/211* (2023.01); *G06F 18/214* (2023.01); *G06N 7/01* (2023.01); *G06N 20/00* (2019.01); *G16H 10/60* (2018.01)

(58) Field of Classification Search
CPC ........ G16H 10/60; G16H 20/10; G06N 20/00; G06N 7/01; G06F 18/211; G06F 18/214
See application file for complete search history.

(56) References Cited

U.S. PATENT DOCUMENTS

| | | | | |
|---|---|---|---|---|
| 4,847,764 | A * | 7/1989 | Halvorson | ........... G06Q 10/087 700/231 |
| 11,645,745 | B2 * | 5/2023 | Wei | ........................ G06N 20/10 382/224 |

(Continued)

FOREIGN PATENT DOCUMENTS

WO WO-2014127234 A1 * 8/2014 ............. G16H 20/10

OTHER PUBLICATIONS

Jason Brownlee, How to Compare Machine Learning Algorithms in Python with Scikit-learn, Aug. 28, 2020, Python Machine Learning (Year: 2020).*

*Primary Examiner* — Kenneth Bartley
(74) *Attorney, Agent, or Firm* — Invoke

(57) ABSTRACT

Methods, systems, and computer-readable media are disclosed that the likelihood that a medical order for multiple pharmaceutical drugs may be stolen or diverted. Generally, a current data set for a medical order for pharmaceutical drugs is received. Each of the drugs is associated with a set of features. An impact score is generated for each of the features for each drug based on historical effects. Test data is also used to evaluate the diversion prediction accuracy of a plurality of machine learning models, when compared to historical diversion data for the drugs. The most accurate machine learning model is utilized to make a diversion probability prediction for those features having the highest impact scores, for the drugs in the medical order. A recommended action is generated and provided based on the diversion probability.

24 Claims, 7 Drawing Sheets

300

310 — RECEIVE A SET OF CURRENT DATA ASSOCIATED WITH AN ORDER

320 — GENERATE AN IMPACT SCORE

330 — IDENTIFY A SET OF IMPACTFUL FEATURES

340 — USING A PLURALITY OF MACHINE LEARNING MODELS, GENERATE AT LEAST ONE PREDICTION FOR EACH OF THE PLURALITY OF MACHINE LEARNING MODELS

350 — DETERMINE THAT A FIRST MACHINE LEARNING MODEL IS MORE ACCURATE THAN EACH OF THE REMAINING MACHINE LEARNING MODELS

360 — USE THE FIRST MACHINE LEARNING MODEL TO DETERMINE THE PROBABILITY OF DIVERSION FOR THE ORDER

370 — GENERATE A REPORT

(51) Int. Cl.
    *G06N 20/00*       (2019.01)
    *G16H 10/60*       (2018.01)

(56)            References Cited

U.S. PATENT DOCUMENTS

| | | | |
|---|---|---|---|
| 11,721,430 B1* | 8/2023 | Schroeder | G16H 20/13 |
| | | | 705/2 |
| 12,125,573 B2* | 10/2024 | Abal | G16H 20/13 |
| 2011/0161108 A1* | 6/2011 | Miller | G06Q 30/0185 |
| | | | 705/3 |
| 2011/0256545 A1* | 10/2011 | Guo | C12Q 1/6886 |
| | | | 536/23.1 |
| 2013/0282392 A1* | 10/2013 | Wurm | G06Q 10/087 |
| | | | 705/2 |
| 2015/0046181 A1* | 2/2015 | Adjaoute | G06Q 10/10 |
| | | | 705/2 |
| 2015/0170306 A1* | 6/2015 | Harper | G06Q 30/018 |
| | | | 705/2 |
| 2015/0324542 A1* | 11/2015 | Hoffman | G16H 50/30 |
| | | | 705/2 |
| 2015/0339456 A1* | 11/2015 | Sprintz | G16H 50/30 |
| | | | 705/3 |
| 2017/0083681 A1* | 3/2017 | Sprintz | G16H 20/10 |
| 2017/0109497 A1* | 4/2017 | Tribble | G16H 70/40 |
| 2018/0039736 A1* | 2/2018 | Williams | G16H 10/60 |
| 2018/0247703 A1* | 8/2018 | D'Amato | G16H 20/17 |
| 2019/0244699 A1* | 8/2019 | Loebig | G16H 20/13 |
| 2019/0355461 A1* | 11/2019 | Kumar | G16H 10/60 |
| 2020/0294643 A1* | 9/2020 | Culbertson | G16H 20/13 |
| 2021/0225521 A1* | 7/2021 | Bostic | G16H 15/00 |
| 2021/0249121 A1* | 8/2021 | Burgess | G16H 20/13 |
| 2021/0287774 A1* | 9/2021 | Curtiss | G16H 70/60 |
| 2021/0295971 A1* | 9/2021 | Mills | G16H 40/67 |
| 2022/0068501 A1* | 3/2022 | Gholami | G16H 70/40 |

* cited by examiner

300

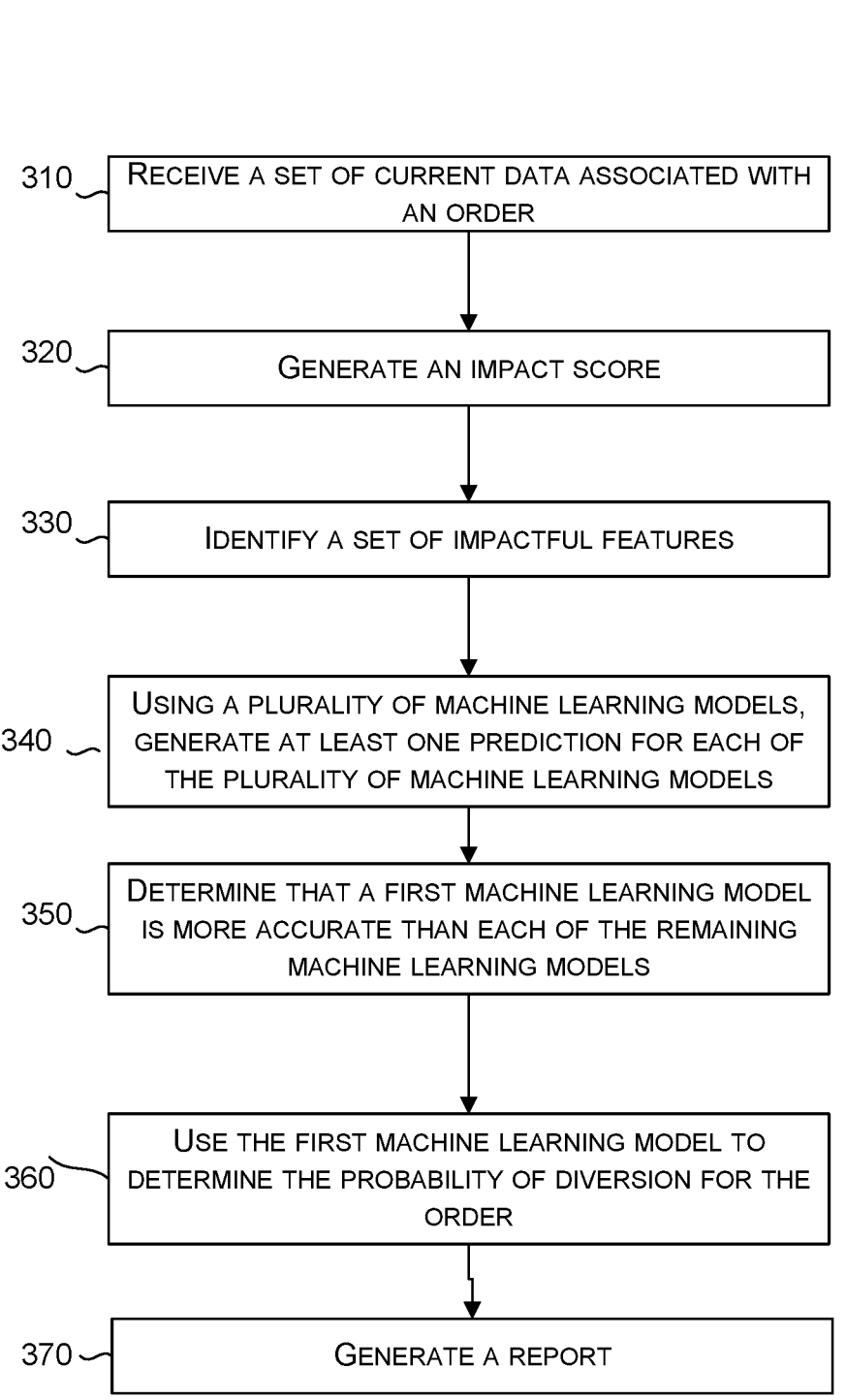

310 — RECEIVE A SET OF CURRENT DATA ASSOCIATED WITH AN ORDER

320 — GENERATE AN IMPACT SCORE

330 — IDENTIFY A SET OF IMPACTFUL FEATURES

340 — USING A PLURALITY OF MACHINE LEARNING MODELS, GENERATE AT LEAST ONE PREDICTION FOR EACH OF THE PLURALITY OF MACHINE LEARNING MODELS

350 — DETERMINE THAT A FIRST MACHINE LEARNING MODEL IS MORE ACCURATE THAN EACH OF THE REMAINING MACHINE LEARNING MODELS

360 — USE THE FIRST MACHINE LEARNING MODEL TO DETERMINE THE PROBABILITY OF DIVERSION FOR THE ORDER

370 — GENERATE A REPORT

FIG. 3

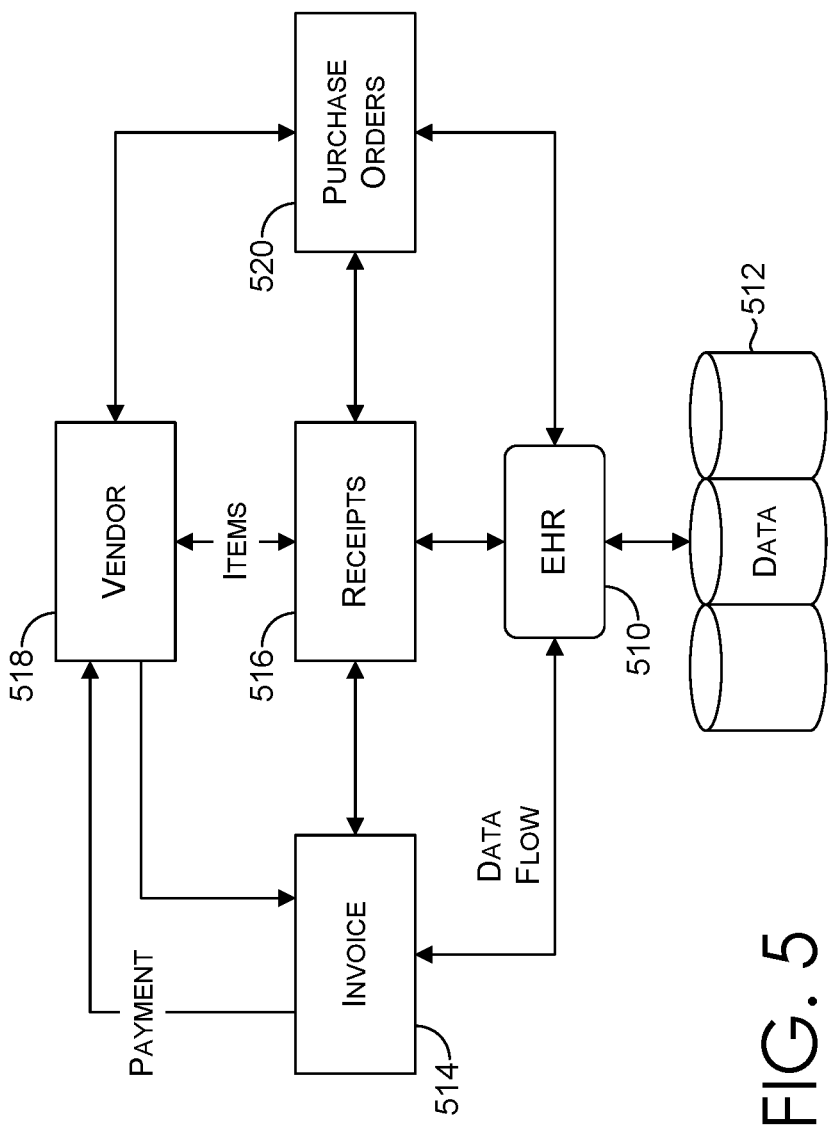
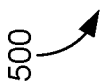
FIG. 5

INTELLIGENT SYSTEM FOR AUTOMATICALLY TESTING AND SELECTING FROM MULTIPLE DATA MODELS FOR ACCURATE DIVERSION PREDICTION

BACKGROUND

Medication diversion is prevalent at all levels in health care organizations. The extent of this diversion can range from low cost uncontrolled medicines to costly controlled substances. The costs of diversion can be in the billions of dollars per user, and the costs to the patient safety can be immeasurable. While this diversion has wide-spread prevalence in the United States health system, there is significant variation in approaches to detecting and deterring diversion. Current solutions are rudimentary, reactive (post-diversion measures), and/or physically deterrent in nature. Further, current solutions are implemented ad-hoc and without any consistency. There are no current solutions available that utilize data models to accurately and proactively predict diversion in advance to specifically manage those items having a highest likelihood of diversion. A new technological solution is needed to accurately and proactively predict diversion in advance to specifically manage those items having a highest likelihood of diversion along all points within a supply, handling, and delivery chain.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims as supported by the Specification, including the Detailed Description.

One aspect of the present disclosure relates to a system for determining a probability of diversion of an order for a plurality of pharmaceutical drugs. The system may include one or more hardware processors configured by machine-readable instructions. In embodiments, a set of current data associated with an order for a plurality of pharmaceutical drugs is received from an electronic health record system. Each of the plurality of pharmaceutical drugs are associated with a set of features. An impact score for each feature of the set of features is generated based on a historical effect each feature has had on the probability of diversion for each of the plurality of pharmaceutical drugs. In embodiments, the method comprises identifying a set of impactful features wherein the impact score at least meets a predetermined threshold. Using a plurality of machine learning models, a prediction is generated for each of the machine learning models. The plurality of machine learning models each predict an effect of the set of impactful features on the probability of each of the plurality of pharmaceutical drugs based on a set of training data. In embodiments, it is determined that a first machine learning model is more accurate than each other machine learning model based on a comparison of the prediction to a test data set associated with a set of historical diversion data for each of the plurality of pharmaceutical drugs. The first machine learning model is used to determine the probability of diversion for the order based on the set of impactful features, and the set of current data associated with the order for the plurality of pharmaceutical drugs. A report comprising at least the probability of diversion for the order and a recommended action is then generated.

Another aspect of the present disclosure relates to a computer-implemented method for determining a probability of diversion of an order for a plurality of pharmaceutical drugs. In embodiments, a set of current data associated with an order for a plurality of pharmaceutical drugs is received from an electronic health record system. Each of the plurality of pharmaceutical drugs are associated with a set of features. An impact score for each feature of the set of features is generated based on a historical effect each feature has had on the probability of diversion for each of the plurality of pharmaceutical drugs. In embodiments, a set of impactful features which have an impact score that at least meets a predetermined threshold are identified. Using a plurality of machine learning models, a prediction is generated for each of the machine learning models. The plurality of machine learning models each predict an effect of the set of impactful features on the probability of each of the plurality of pharmaceutical drugs based on a set of training data. In embodiments, it is determined that a first machine learning model is more accurate than each other machine learning model based on a comparison of the prediction to a test data set associated with a set of historical diversion data for each of the plurality of pharmaceutical drugs. The first machine learning model is used to determine the probability of diversion for the order based on the set of impactful features, and the set of current data associated with the order for the plurality of pharmaceutical drugs. A report comprising at least the probability of diversion for the order and a recommended action is then generated.

Yet another aspect of the present disclosure relates to a non-transitory computer-readable storage medium having instructions embodied thereon, the instructions being executable by one or more processors to perform a method for determining a probability of diversion of an order for a plurality of pharmaceutical drugs. In embodiments, a set of current data associated with an order for a plurality of pharmaceutical drugs is received from an electronic health record system. Each of the plurality of pharmaceutical drugs are associated with a set of features. An impact score for each feature of the set of features is generated based on a historical effect each feature has had on the probability of diversion for each of the plurality of pharmaceutical drugs. In embodiments, a set of impactful features which have an impact score that at least meets a predetermined threshold are identified. Using a plurality of machine learning models, a prediction is generated for each of the machine learning models. The plurality of machine learning models each predict an effect of the set of impactful features on the probability of each of the plurality of pharmaceutical drugs based on a set of training data. In embodiments, it is determined that a first machine learning model is more accurate than each other machine learning model based on a comparison of the prediction to a test data set associated with a set of historical diversion data for each of the plurality of pharmaceutical drugs. The first machine learning model is used to determine the probability of diversion for the order based on the set of impactful features, and the set of current data associated with the order for the plurality of pharmaceutical drugs. A report comprising at least the probability of diversion for the order and a recommended action is then generated.

BRIEF DESCRIPTION OF THE DRAWINGS

Illustrative embodiments of the present disclosure are described in detail below with reference to the attached drawing figures, and wherein:

FIG. 3 illustrates an example method for determining a probability of medication diversion, in accordance with one or more implementations;

FIG. 5 illustrates a delay predicting system configured for tracking information related to supply orders, in accordance with one or more implementations;

DETAILED DESCRIPTION

The subject matter of the present disclosure is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described. Further, it will be apparent from this Detailed Description that the technological solutions disclosed herein are only a portion of those provided by the present disclosure. As such, the technological problems, solutions, advances, and improvements expressly referenced and explained should not be construed in a way that would limit the benefits and application of embodiments of the present disclosure.

Embodiments herein provide a technological solution that addresses, solves, and overcomes the technological problems and/or shortcomings found in systems used to track inventory of pharmaceutical drugs and predict potential areas of loss or theft. Among other improvements, embodiments herein describe technologies that allow for electronic health records (EHR) systems to determine orders for pharmaceutical drugs which have varying risks of diversion. Using this information, the EHR system is able to prioritize computing power to focus on tracking or monitoring the orders having higher risk of diversion and divert power and memory away from those having a lower risk of diversion.

Figure 1:
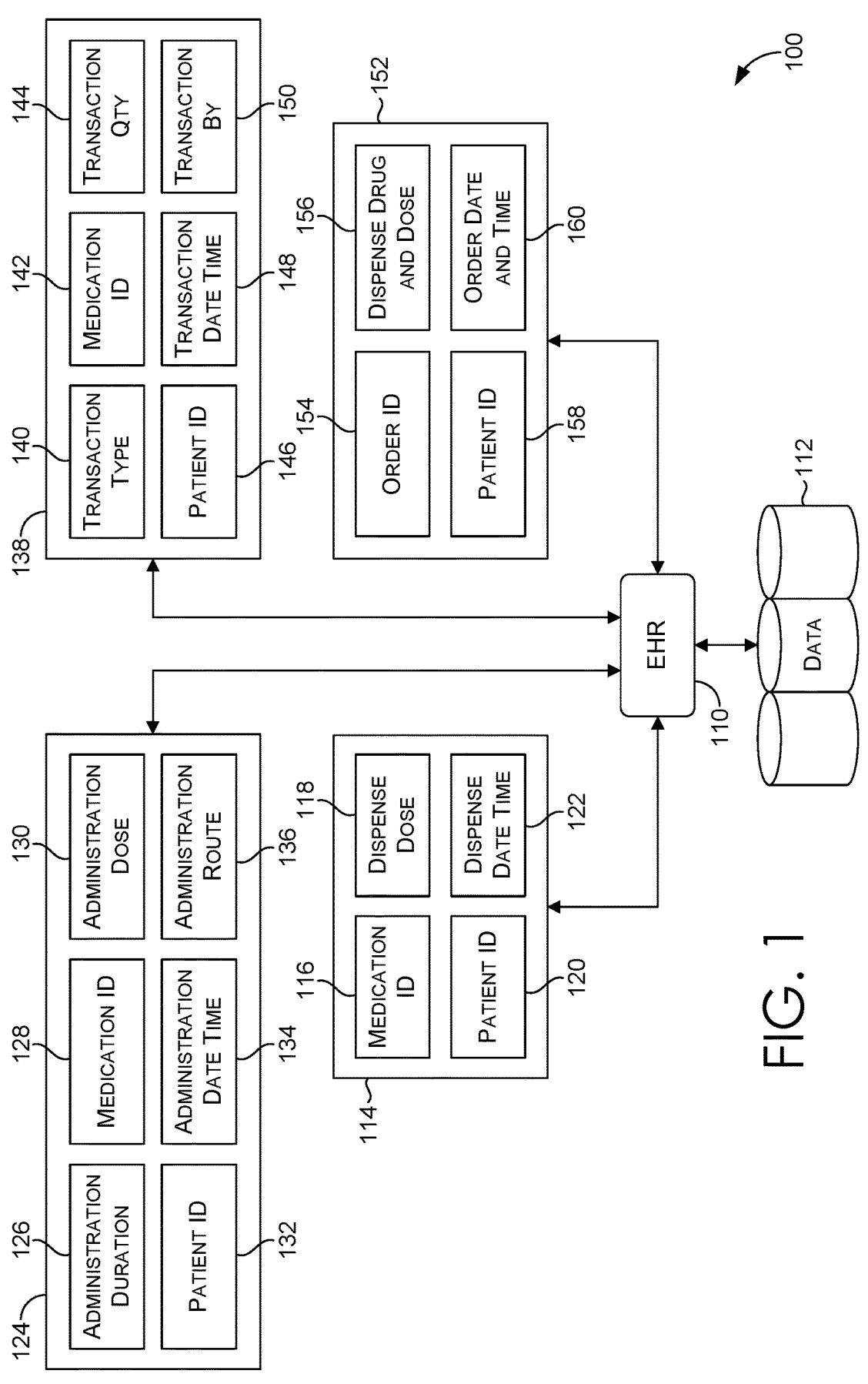
FIG. 1 illustrates a computing environment configured for storing information related to determining a probability of medication diversion, in accordance with one or more implementations.

FIG. 1 illustrates a computing environment 100 for predicting a probability of diversion for an order of pharmaceutical drugs, in accordance with one or more implementations. In some implementations, computing environment 100 may include a medication module 114. The medication module 114 may store, manage, monitor, and update information related to at least a medication identifier ("medication ID") 116, a dispense dose 118, a patient ID 120, and/or a dispense date and time 122. The computing environment 100 may also include an order module 152. The order module 152 may store, manage, monitor, and update information related to at least an order ID 154, a dispense drug and dose 156, a patient ID 158, and/or an order date and time 160. The terms "drug", "medication", "pharmaceutical", and/or any combination thereof are used herein as having the same of similar meaning. The use of the different terms may be employed to avoid confusion that might occur due to similar sounding features, functions, modules, components, and the like herein. The computing environment 100 may also include a transaction module 138. The transaction module 138 may store, manage, monitor, and update information related to at least a transaction type 140, a medication ID 142, a transaction quantity 144, a patient ID 146, a transaction date and time, and/or and identifier of a party (entity, user, or person) whom initiated a particular transaction. Finally, the computing environment 100 may also include an administration module 124. The administration module 124 may store, manage, monitor, and update information related to at least an administration duration 126, a medication ID 128, an administration dose 130, a patient ID, 132, an administration date and time 134, and/or an administration route 136. In further embodiments, each module of the computing environment 100 may include additional relevant information. The medication module 114 may also store information such as a drug type or drug cost to indicate for example that a particular pharmaceutical drug is an opioid and has a cost to patient of X amount of dollars. Similarly, the order module 152 may include information indicating the market name of each drug included on a particular order having a particular order ID 154. The order module 152 may also include total market cost for an order, or a designated pharmacy to which the order is being issued. In embodiments, the transaction module 138 may include information indicating the individual who issued an order. Finally, the administration module may also include any other information determined to be relevant to the administration of medication. Each of the medication module 114, order module 152, the transaction module 138, and/or the administration module may include any other information related to determining a probability of medication diversion.

In embodiments, each of the medication module 114, the order module 152, the transaction module 138, and/or the administration module 124 may be communicatively linked to an EHR (electronic health record) system 110, which is communicatively linked to a database 112. In further embodiments, each of the medication module 114, the order module 152, the transaction module 138, and/or the administration module 124 may each be stored in or in association with a database 112 associated with the EHR system 110. Each module of the computing environment 100 may also be communicatively coupled to or stored in association with each of the other modules of the computing environment 100. In further embodiments, all of the information stored in association with the modules of the computing environment 100 may be manually entered or regularly updated from outside sources. This information may be monitored and updated at regular intervals, such as hourly or day, for example.

In embodiments, portions of or all of the information stored in one or more of or all of the modules of the computing environment 100 may be used in the process of determining a probability of diversion. For example, information such as the administration route 136, the dispense dose 118, and the medication ID 128 may, together, alone, or in various combinations, represent features which may increase, decrease, or cause no change for a probability of diversion for a particular pharmaceutical drug and/or a particular order having one or more pharmaceutical drugs. In embodiments, features may be comprised of data related to a pharmaceutical drug, or an order for pharmaceutical drugs. For example, a feature may be a particular cost for a pharmaceutical drug, a type associated with the pharmaceutical drug, such as opioid, or an administration dosage. A feature for an order may be a total cost for the order, an issuing facility for the order, or a pharmacy to which the order was issued. In embodiments, an order for a plurality of pharmaceutical drugs. The order may be issued to a pharmacy internal to a facility, to an outside pharmacy, or any other entity from which the facility may purchase or receive pharmaceutical drugs. Additionally, in some embodiments, each of the medication ID 128, the medication ID 116, and the medication ID 142 may represent unique medication IDs stored in each associated module shown in FIG. 1. In other embodiments, each of the medication ID 128, the medication ID 116, and/or the medication ID 142 may represent the same medication ID. Thus, this may represent at least some redundant data stored in various modules in order to ensure data integrity, in some embodiments. Additionally, this may represent that information may be combined from different sources to create a single source or table of information.

In embodiments, the information stored in each of these modules may be used to track information related to various pharmaceutical drugs, patients, orders, and transactions. For example, the patient ID 132, the medication ID 116, and the order ID 154 may be used to indicate a particular medication such as ibuprofen, or a particular type of medication such as opioids. Additionally, similar to the medication ID above, each of the medication ID 128, the medication ID 116, and the medication ID 142 may represent unique medication IDs stored in each associated module. In further embodiments, each of the medication ID 128, the medication ID 116, and the medication ID 142 may represent the same medication ID. This may represent at least some redundant data stored in various modules in order to ensure data integrity, in aspects. Additionally, this may represent that information may be combined from different sources to create a single source or table of information.

Having described computing environment 100 and components thereof, it will be understood by those of ordinary skill in the art that computing environment 100 is but one example of a suitable system and is not intended to limit the scope of use or functionality of the present disclosure. Similarly, computing environment 100 should not be interpreted as imputing any dependency and/or any requirements with regard to each component and combination(s) of components illustrated in FIG. 1. It will be appreciated by those of ordinary skill in the art that the location of components illustrated in FIG. 1 is an example, as other methods, hardware, software, components, and devices for establishing a communication links between the components shown in FIG. 1 may be utilized in implementations of the present disclosure. It will be understood to those of ordinary skill in the art that the components may be connected in various manners, hardwired or wireless, and may use intermediary components that have been omitted or not included in FIG. 1 for simplicity's sake. As such, the absence of components from FIG. 1 should not be interpreted as limiting the present disclosure to exclude additional components and combination(s) of components. Moreover, though components are represented in FIG. 1 as singular components, it will be appreciated that some embodiments may include a plurality of devices and/or components such that FIG. 1 should not be considered as limiting the number of a device or component.

Figure 2:
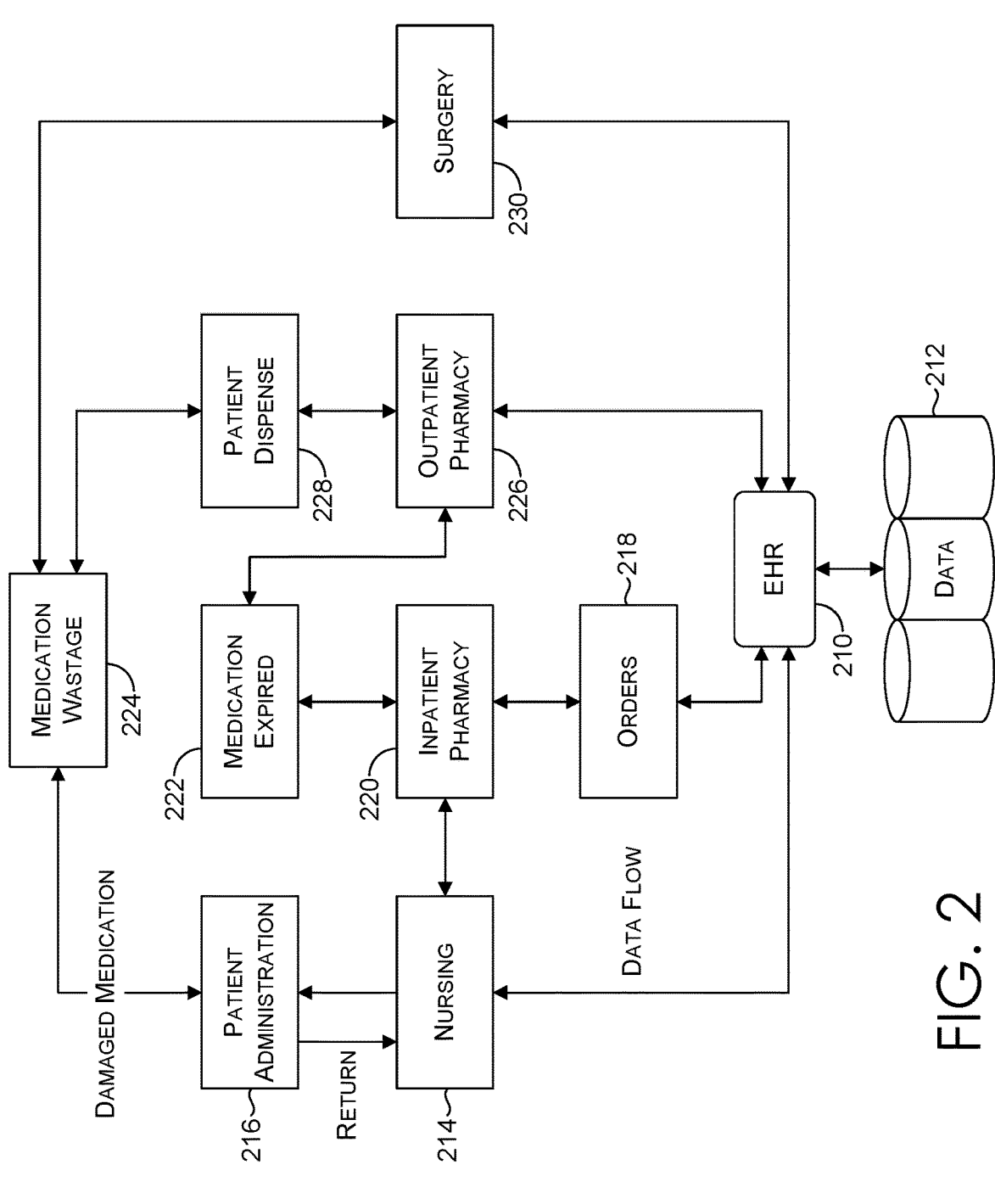
FIG. 2 illustrates a system for tracking medication diversion, in accordance with one or more implementations.

FIG. 2 illustrates a tracking system 200 for monitoring medicines at all points in ordering and handling for diversion prediction. This medication tracking system 200 tracks information related to pharmaceutical drugs which a facility has previously ordered but since used or consumed, pharmaceutical drugs which have been ordered and which the facility currently has possession of, pharmaceutical drugs for which an order has been issued but the facility has not yet obtained, and/or pharmaceutical drugs for which an order has not yet issued. All of this may be stored in association with an EHR system 210 or in a database 212 associated with the EHR system 210. In embodiments, the tracking system 200 may track and store information associated with the transport and use of pharmaceutical drugs. For example the tracking system 200 may determine that pharmaceutical drugs currently stored at a facility were distributed to the nursing 214 department. Said pharmaceutical drugs underwent patient administration 216, wherein the patient was given physical possession of the pharmaceutical drugs and/or the pharmaceutical drugs were ingested by the patient using any route of administration. Alternatively, the tracking system 200 may determine that the pharmaceutical drugs were damaged, and therefore resulted in medication wastage 224. Or, the tracking system may determine that the medication was returned to the nursing 214 department.

In embodiments, the tracking system 200 may determine that the orders 218 for pharmaceutical drugs were issued to an inpatient pharmacy 220. The pharmaceutical drugs associated with these orders 218 may be distributed to the nursing 214 department, or it may be determined that the pharmaceutical drugs associated with the order 218 have expired with regard to shelf life and/or therapeutic stability of the active compounds or formulation. In embodiments in which is the tracking system 200 determines that the pharmaceutical drugs have expired, the tracking system 200 can electronically document, flag or "mark" the pharmaceutical drugs in the inpatient pharmacy 220 as having a medication expired 222 status. In further embodiments, the pharmaceutical drugs that have been marked as medication expired 222 may correspond to the orders 218 that were transmitted to an outpatient pharmacy 226. Because the pharmaceutical drugs in the inpatient pharmacy 220 are marked as medication expired 222, the order must be sent to an outpatient pharmacy 226 in order to obtain unexpired medications to replenish the inpatient pharmacy 220. The pharmaceutical drugs may undergo patient dispense 228 instructions, wherein patients that are not located at the facility can pick up their pharmaceutical drugs for the corresponding order. In embodiments, these pharmaceutical drugs that undergo patient dispense 228 instructions may also be marked as medication wastage 224 by the tracking system 200. The tracking system 200 may also determine that pharmaceutical drugs are distributed to or used by the surgery 230 department.

In embodiments, at any point that the tracking system 200 cannot determine a current status of a pharmaceutical drug, the tracking system 200 may intuitively determine that said pharmaceutical drug has been diverted. Medication diversion as used herein can indicate any instance that a system, user, or facility physically and/or electronically cannot locate or "loses track" of a pharmaceutical drug, which might be attributed to theft or misplacement, for example. For example, if the tracking system 200 determines that the pharmaceutical drugs associated with an order have been physically distributed to the nursing 214 department specifically for the order to administer to a patient, based on electronic documentation in a workflow or EHR system 210, but that there is no electronic record that patient administration 216 has occurred, the tracking system 200 may mark these pharmaceutical drugs as having been diverted. In embodiments, this determination can happen based on determining that a patient administration 216 was scheduled for a particular date and time, and then determining that the particular date and time has passed without an electronic indication that patient administration 216 has occurred. In another embodiment, the tracking system 200 may detect a diversion by the tracking system 200 determines that a patient administration 216 was scheduled for a particular date that has now passed without an electronic indication that patient administration 216 has occurred. In such an instance, diversion may not be determined until one business day after the missed administration to prevent inaccurate diversion determinations as the business-day-delay acts as a buffer that accounts for modest delays in drug administration due to staff shortages, rescheduling, and/or emergencies. Each instance of a diversion determination is stored in the database 212 associated with the EHR system 210. Additionally, in some embodiments, all information associated with the diverted medication, order, patient, scheduled administration, and the like is also stored in the database 212. This information can include information associated with where in the workflow the tracking system 200 determined that the medication was diverted, such as, in the example above, a diversion occurred at the nursing 214 department. In embodiments, information stored in the modules of computing environment 100 can also be stored in association with this determined medication diversion. All of the information determined by, tracked by, or associated with the tracking system 200 may be used as features when a probability of diversion is determined.

FIG. 3 illustrates a computer-implemented method 300 for determining a probability of diversion of an order for a plurality of pharmaceutical drugs, in accordance with one or more implementations. The operations of the method presented below are intended to be illustrative. In some implementations, the method may be accomplished with one or more additional operations not described, or without one or more of the operations discussed. Additionally, the order in which the operations of the method 300 are illustrated in FIG. 3 and described below is not intended to be limiting unless expressly discussed.

Additionally, the method 300 of FIG. 3 may be performed via one or more of the components and component interactions of previously described FIG. 1 and FIG. 2, and later described in FIGS. 4-7. As such, the method 300 is discussed briefly for brevity, though it will be understood that the previous discussion can be applicable to aspects of the method of FIG. 3. In various embodiments, one or more non-transitory computer-readable storage media having computer-readable instructions or computer-readable program code portions embodied thereon, for execution via one or more processors, may be executed to implement and/or perform one or more of the method 300 shown in FIG. 3. For example, computer-readable instructions or computer-readable program code portions can specify the performance of the method 300, can specify a sequence of steps of the method 300, and/or can identify particular component(s) of a software and/or hardware for performing one or more of the steps of the method 300, in embodiments. The computer-readable instructions or computer-readable program code portions can correspond to an application plugin or an application programming interface (API), in some embodiments. In one embodiment, the plugin or API can implement and/or perform the method 300. As discussed below, the method 300 can be performed using any and all of the software, hardware, modules, and/or component(s), shown in FIGS. 1, 2, and 4-7.

In some implementations, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

FIG. 3 illustrates method 300, in accordance with one or more implementations.

Method 300 may be implemented as a computer-implemented method. In further embodiments, method 300 may be implemented by a computer system having one or more computer storage media storing computer-useable instructions. In even further embodiments, method 300 may be implemented by non-transitory computer-readable media having computer-executable instructions embodied thereon that, when executed, perform a method.

In various embodiments, the method 300 for determining a probability of diversion may comprise, at block 310, receiving, from an electronic health record (EHR) system, a set of current data associated with an order for a plurality of pharmaceutical drugs, each of the plurality of pharmaceutical drugs being associated with a set of features. In some embodiments, the set of features may be retrieved from a database associated with the EHR system. In embodiments, the probability of diversion represents a probability (e.g., value or percentage representing likelihood) that a pharmaceutical drug will be lost, stolen, or misplaced. The set of features can include at least one of a drug type, a drug cost, and/or an average time for delivery. In embodiments, the set of features can be any information stored in or determined by the modules in the computing environment 100, and the tracking system 200. Also as discussed above, features for each of the plurality of pharmaceutical drugs may be any information that is deemed to be potentially relevant to determining a probability of diversion. In embodiments, features may also be related to the order of the plurality of pharmaceutical drugs. For example, a particular order may have features related to a number of drugs ordered in that order, a date and time the order was issued, a particular pharmacy to which the order was issued for fulfillment, and/or any other information deemed by the tracking system 200 to be potentially relevant to the order.

At block 320, an impact score for each feature of the set of features is generated based on a historical effect each feature of the set of features has had on the probability of diversion for each of the plurality of pharmaceutical drugs. In embodiments, the historical effect that each feature of the set of features has had on the probability of diversion is determined based on a percentage increase or decrease of the probability of diversion caused by each feature of the set of features. For example, one of the pharmaceutical drugs included in an order may have the associated features of a price, a drug type, and a dispense dose 118. For example, drug C may be associated with the feature "price", having a category of "expensive" or "inexpensive". The feature "price" describes a purchase cost associated with drug C. In this example, drug C may also be associated with a feature "drug type" having a category "antibiotic". The feature "drug type" can indicate the category or class of the drug, such as the use, application, or action of drug C.

An impact score is determined for each of the price, the drug, the type and the dispense dose 118, specifically based on how each separate or distinct feature has previously affected (increase, decrease, no changes, and magnitude of any change) diversion occurrence as recorded in historical data for other orders having the same or similar price, drug, type, and dispense dose, for example. If the pharmaceutical drug for this example has a drug type of "opioid", it is determined whether the drug type opioid, as a feature, has historically affected the probability of diversion. The magnitude of impact (e.g., value increase/decrease, percentage increase/decrease, magnitude of increase/decrease) the feature of drug type "opioid" has had on the historical probability of diversion is used to generate the impact score for that feature for the pharmaceutical drug in the present order. For example, if the feature of drug type opioid has historically increased the probability of diversion by twenty percent for other historical order having the same or similar feature of drug type opioid, the drug type opioid/feature for the presently evaluated pharmaceutical drug in the order may be assigned an impact score of twenty.

In embodiments, an impact score is generated and assigned for each feature associated with the pharmaceutical drug irrespective of how high or low the impact score may be (relative to other impact scores of other features, for other pharmaceutical drugs). Additionally, the impact score of each feature associated with a particular pharmaceutical drug may be affected by the other features associated with the pharmaceutical drug. In other words, when a specific combination of features are associated with a particular pharmaceutical drug, the impact score for one or more of those features may be summed and/or may exponentially increase, than had only one of those features been present for the particular pharmaceutical drug. For example, drug A has the features of drug type "opioid" and price "expensive." It may be determined that the drug type opioid feature historically increased the probability of diversion by 22 percent and the price expensive feature has historically increased the probability of diversion by 16 percent. Together, drug A would have a summed impact score of 38 percent likelihood of increased diversion, based on those two features. In another example, drug B also has the drug type opioid feature but in combination with the price feature "inexpensive". For drug B, the drug type opioid feature increases the probability of diversion by 22 percent, while the inexpensive feature may also increase the probability of diversion by three percent. Whereas for a pharmaceutical drug having a feature of drug type "non-opioid", a feature of price "expensive" may increase the probability of diversion by 15 percent, a price "inexpensive" feature associated with a pharmaceutical drug having the drug type non-opioid feature may only increase the probability of diversion by three percent.

At block 330, a set of impactful features having an impact score that at least meets a predetermined threshold is identified. In embodiments, the amount that the drug type opioid feature increases the probability of diversion is taken into account. For example, if the drug type opioid feature only increases the probability of diversion by five percent, then the drug type opioid feature may not be determined to be an impactful feature. On the other hand, if the drug type opioid feature increase the probability of diversion by 20 percent, then the drug type opioid feature may be determined to be an impactful feature. In embodiments, the threshold set for whether an increase or decrease in historical affect renders a feature value/category as impactful may be predetermined by a user. For example, a user may determine that only features having a 10 percent increase or decrease can be impactful features. Therefore if any feature has historically increased or decreased the probability of diversion by at least 10 percent, that feature is determined to be an impactful feature for that pharmaceutical drug by the tracking system 200.

At block 340, a plurality of machine learning models are used to generate a prediction for each machine learning model of the plurality of machine learning models, wherein the prediction indicates the predicted effect (e.g., increase, decrease, or no change) that the set of impactful features is expected to have on the probability of diversion for each of the plurality of pharmaceutical drugs in the order, based on a set of training data. In embodiments, each machine learning model generates a prediction using its own specific algorithms, learning methods and restraints. Additionally, each machine learning model of the plurality of machine learning models generates its own prediction based on the same set of training data. This allows for each of the plurality of machine learning models to be compared against one another using a common denominator: the set of training data.

In embodiments, the set of training data is comprised of a plurality of data stored in association with the EHR system. This data can include the information determined and monitored by the tracking system 200, and may also include any information stored in the modules of the computing environment 100. The set of training data is comprised of this known, historical information and used by each of the plurality of computer learning models to generate predictions. As discussed below, these predictions are then tested against a set of test data. In embodiments, the plurality of machine learning models can be wholly distinct machine learning models such as neural network machine learning, or random forest machine learning. In further embodiments, the machine learning models may all be, for example, but have differing parameters or learning methods. In embodiments, each machine learning model of these machine learning models process the training data which comprises historical pharmaceutical drug diversion data.

At block 350, a first machine learning model of the plurality of machine learning models is determined to be more accurate than each of the other machine learning models of the plurality of machine learning models, based on a comparison of the predictions of each of the plurality of machine learning models using the training data relative to the test data set (e.g., historical diversion data). The test data set is associated with a set of historical diversion data for each of the plurality of pharmaceutical drugs being evaluated in the present order. In further embodiments, the test data may be comprised of a set of result data directly related to the training set. The predictions output from each of the plurality of machine learning models after ingesting training data are evaluated by determining whether or not those predictions are accurate, quantified using a percentage, value, or magnitude, in view of the test data, such as historical diversion data. In other words, based on the historical diversion data and/or result data of the test data, it's determined whether any of the models were able to produce, by ingesting the training data, a prediction that is value/metric similar to the test data, such as result data and/or historical information related to the set of impactful features. This historical information is then associated with the set of test data in that in the past, the historical information resulted in a particular outcome of diverted or not diverted. Therefore when evaluating the training data outcomes from the model against the test data, the outcome of the prediction is known, so that a most accurate prediction can be determined. In embodiments, the set of historical diversion data associated with each of the plurality of pharmaceutical drugs is retrieved from the database associated with the electronic health record system. In further embodiments, the historical diversion data may be received from at least one of computing environment 100 or tracking system 200. As discussed above, computing environment 100 and tracking system 200 store information related to pharmaceutical drugs and previous instances of diversion.

At block 360, the first machine learning model is used to determine the probability of diversion for the order based on the set of impactful features and the set of current data associated with the order for the plurality of pharmaceutical drugs. In further embodiments, determining the probability for the order further comprises using the set of impactful features to generate the probability of diversion for each of the plurality of pharmaceutical drugs, and based on the probability of diversion for each of the plurality of pharmaceutical drugs, the probability for the order is generated. Additionally, the first machine learning model may use features associated with the order when determining a probability of diversion. These features associated with the order may be distinct from the features associated with each of the plurality of pharmaceutical drugs. In further embodiments, the set of current data is specific to the pharmaceutical drugs listed in the order and is specific to the order itself.

At block 370, a report comprising at least the probability of diversion for the order, and a recommended action is then generated. The recommended action generated may be information specific to the order, or to particular pharmaceutical drugs listed in the order. For example, if the probability of diversion is determined to be above a certain threshold, the report might recommend that the order be tracked more thoroughly than average. The recommended action could also include recommending that an order be sent to a particular pharmacy or that some of the pharmaceutical drugs be removed from the order or split up between multiple orders. If the probability of diversion is determined to be below a certain threshold, the recommended action could be to send the order as is.

Additionally, if a particular order is determined to be below a threshold the recommend action could comprise a recommendation to devote computing resources to tracking a different order. This way, the EHR and associated systems can save processing power and work more efficiently to monitor the orders which have a higher risk of diversion. In further embodiments, the probability of diversion for the order is associated with a risk tier. Additionally, a first risk tier may be associated with a first range of probability of diversion and a second risk tier may be associated with a second range of probability of risk. Additionally, the In further embodiments, the report may comprise a table having at least three columns associated with the probability of diversion, the recommended action, and the risk tier. The report may take the form of a notification transmitted to a user computing device, wherein the notification causes a graphical user interface comprising the table to display on the user computing device. In further embodiments, the report may also be printed or provided in other physical formats.

Figure 4:
FIG. 4 illustrates a supply predicting system for predicting delays in supply orders, in accordance with one or more implementations.

Moving to FIG. 4, a supply predicting computing environment 400 for predicting supply needs for a facility or set of facilities is illustrated, in accordance with one or more implementations. In embodiments, the supply predicting system 400 monitors and tracks information related to a plurality of supply orders and pharmaceutical drugs as they move through the supply chain and throughout a facility's system. In embodiments, the supply predicting system is communicatively coupled to an EHR system 410 and a database 412 associated with the EHR. In further embodiments, the delay predicting system is stored in or in association with the EHR system 410.

The supply predicting system 400 is configured to track information related to a plurality of pharmaceutical drugs as they are used, wasted, misplaced, stolen, expired, etc. The supply predicting system 400 determines what pharmaceutical drugs are stored at particular facilities, what pharmaceutical drugs have been ordered, and what pharmaceutical drugs are in demand, or out of stock at particular facilities. In embodiments, the supply predicting system determines what pharmaceutical drugs have been ordered by the purchase orders 422. The supply predicting system 400 may determine which of these plurality of drugs are received items 416. In embodiments, received items 416 are determined by comparing the amount of pharmaceutical drugs included in a purchase order to the amount of pharmaceutical drugs received by the actual facility. If there are discrepancies between these amounts, the discrepancy is noted by the supply predicting system 400. Further, the supply predicting system 400 may analyze the invoice 414 to determine the amount of pharmaceutical drugs ordered by the facility. Once items have been received by the facility, the supply predicting system may also constantly monitor the item consumption 418 and the wastage 420.

As discussed below, the information monitored and determined by the supply predicting system may be stored in a database 412 associated with the EHR 410 and be stored in the order computing environment 600. All of this information may be used by the supply predicting system to predict the needs for future purchase orders 422 for pharmaceutical drugs. Similar to the systems and methods discussed in association with FIGS. 1-3, the plurality of information determined and monitored by the supply predicting system 400 may be used as features when predicting a pharmaceutical drug supply need for a facility. For example, it may be determined that a particular pharmaceutical drug having features of inexpensive and high quantity is often wasted or lost between the purchase orders 422 being created and the pharmaceutical drugs being determined to be receive items 416.

These particular features may indicate that a pharmaceutical drug associated with these features have a higher probability of being lost and therefore the facility may need to prepare to order more of said pharmaceutical drugs. In further embodiments, it may be determined that the item consumption 418 rate of pharmaceutical drugs having a particular set of features is higher than that of pharmaceutical drugs not associated with the particular set of features. In embodiments, the item consumption 418 rate of pharmaceutical drugs may be measured over a period of time. Using this information the supply prediction system may predict that a higher quantity of the pharmaceutical drugs will be needed in the future. Similar to the subject matter discussed in FIGS. 1-3 above, the features associated with the information determined and monitored by the supply predicting system may be determined to be impactful features if they historically affect the demand for a pharmaceutical drug associated with those features. The supply predicting system may use various machine learning modules to predict a future need for pharmaceutical drugs based on features associated with the pharmaceutical drugs.

FIG. 5 illustrates an additional embodiment comprising a delay predicting system 500. The delay predicting system 500 may use information related to purchase orders 520, receipts 516 invoices 514, and vendors 518 to determine if orders for pharmaceutical drugs are delayed, and by what amount they are delayed. The delay predicting system may determine features related to various pharmaceutical drugs and various orders, and whether or not these features affect the probability that purchase orders 520 will be delayed. Similar to the subject matter discussed in FIGS. 1-3, the delay predicting system may use machine learning technology to determine if a current or future order will be delayed, based on the features determined by the delay predicting system. In embodiments, the delay predicting system 500 may determine a historical pattern of delays associated with the features.

Figure 6:
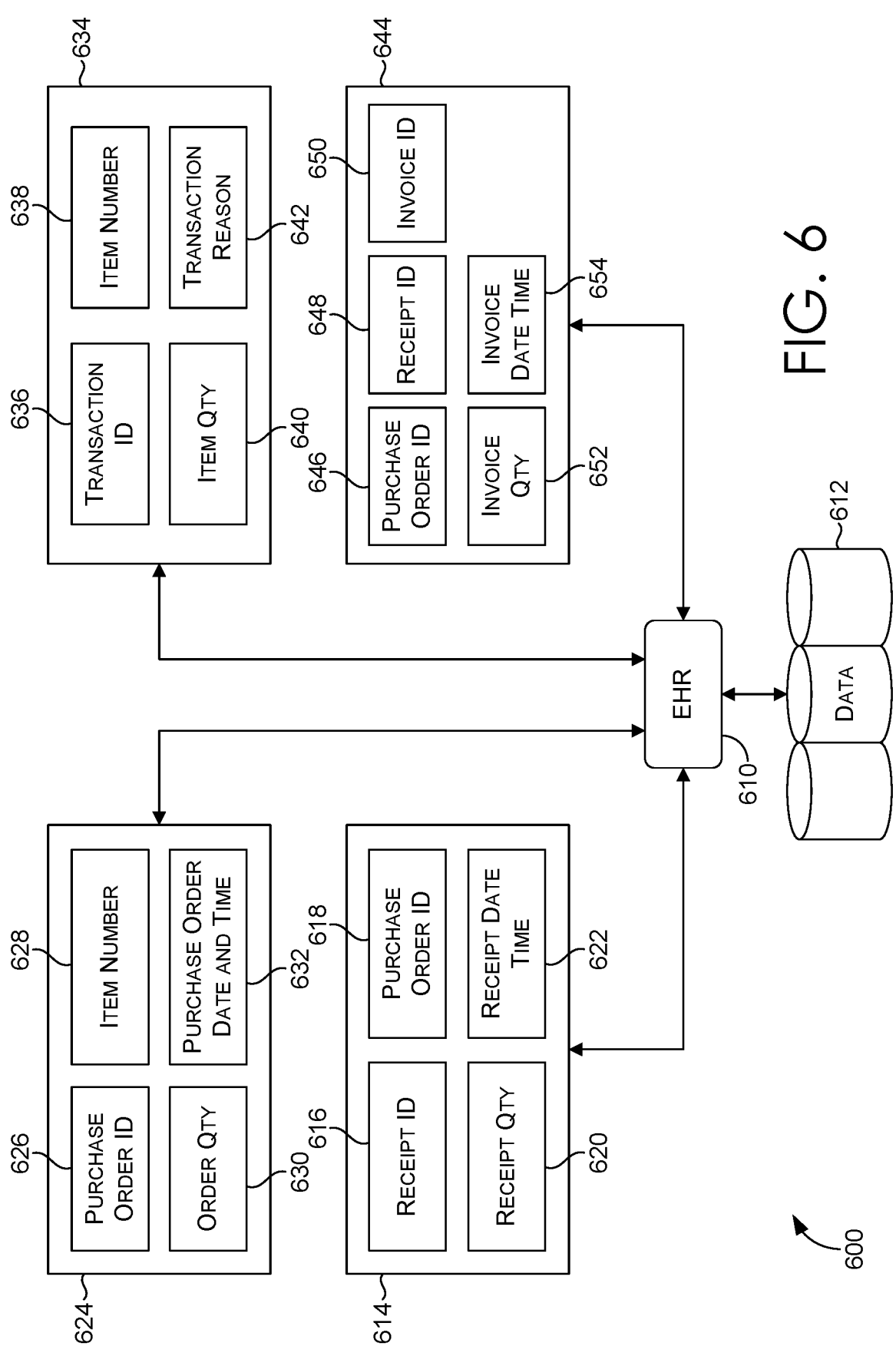
FIG. 6 illustrates an order computing environment configured for storing information related to supply orders, in accordance with one or more implementations.

FIG. 6 illustrates an order computing environment configured for storing information related to supply orders. In some implementations, order computing environment 600 may include a receipt module 614. The receipt module 614 may include information related to at least a receipt ID 616, a purchase order ID 618, a receipt quantity 620, and a receipt date and time 622. The order computing environment 600 may also include an order module 624. The order module 624 may store, manage, monitor, and update information related to at least a purchase order ID, an item number, an order quantity, and a purchase order date and time 632. In embodiments, the order computing environment 600 may also include a transaction module 634. The transaction module 634 may store, manage, monitor, and update information related to at least a transaction ID 636, an item number 638, an item quantity 640, and a transaction reason 642. In further embodiments, the order computing environment 600 may also include an invoice module 644. The invoice module 644 may store, manage, monitor, and update information related to at least a purchase order ID 646, a receipt ID 648, an invoice ID 650, an invoice quantity 652, and an invoice date and time 654. In further embodiments, each module of the order computing environment 600 may store, manage, monitor, and update additional information determined or monitored by the supply predicting system 400 and the delay predicting system 500.

In embodiments, each of the receipt module 614, order module 624, transaction module 634, and invoice module 644 may be communicatively linked to an EHR system 610, which is communicatively linked to a database 612. In further embodiments, each of the receipt module 614, order module 624, transaction module 634, and invoice module 644 may be stored in or in association with the database 612 associated with the EHR system 610. In further embodiments, all of the information stored in association with the modules of the order computing environment 600 may be manually entered, or regularly updated from outside sources. This information may be monitored and updated at regular intervals such as hourly or day.

In embodiments, all of the information stored in each of the modules of the order computing environment 600 may be used in the process of predicting a supply demand, or a supply delay as discussed in association with FIGS. 4 and 5. Additionally, in embodiments, each of purchase order ID 626, purchase order ID 646, and purchase order ID 618 may represent unique purchase order IDs stored in each associated module. In further embodiments, each of receipt ID 618 and receipt ID 648 may represent unique receipt IDs stored in each associated module. In further embodiments, each of item number 628 and item number 638 may represent unique item numbers stored in each associated module. In embodiments each instance above may indicate the same purchase order ID, receipt ID, or item number. This may represent redundant data stored in various modules in order to ensure data integrity. Additionally, this may represent that information may be combined from different sources to create a single source or table of information.

Figure 7:
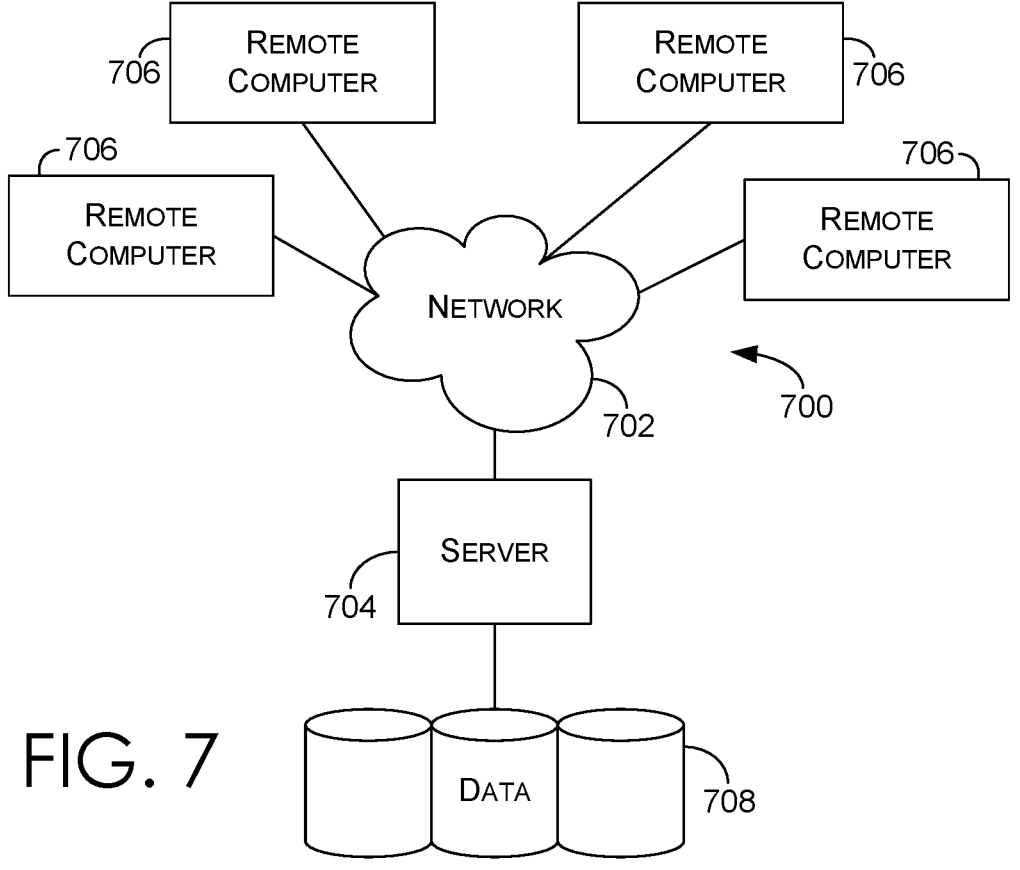
FIG. 7 illustrates an example computing environment, in accordance with one or more implementations.

Hereinafter, an example computing environment is described with regard to the systems, methods, and computer-media described hereinabove. Turning to FIG. 7, an example computing environment is depicted, in accordance with an embodiment of the present disclosure. It will be understood by those of ordinary skill in the art that the example computing environment 700 is just one example of a suitable computing environment and is not intended to limit the scope of use or functionality of the present disclosure. Similarly, the computing environment 700 should not be interpreted as imputing any dependency and/or any requirements with regard to each component and combination(s) of components illustrated in FIG. 7. It will be appreciated by those having ordinary skill in the art that the connections illustrated in FIG. 7 are also examples as other methods, hardware, software, and devices for establishing a communications link between the components, devices, systems, and entities, as shown in FIG. 7, may be utilized in implementation of the present disclosure. Although the connections are depicted using one or more solid lines, it will be understood by those having ordinary skill in the art that the example connections of FIG. 7 may be hardwired or wireless, and may use intermediary components that have been omitted or not included in FIG. 7 for simplicity's sake. As such, the absence of components from FIG. 7 should not be interpreted as limiting the present disclosure to exclude additional components and combination(s) of components. Moreover, though devices and components are represented in FIG. 7 as singular devices and components, it will be appreciated that some embodiments may include a plurality of the devices and components such that FIG. 7 should not be considered as limiting the number of a device or component.

Continuing, the computing environment 700 of FIG. 7 is illustrated as being a distributed environment where components and devices may be remote from one another and may perform separate tasks. The components and devices may communicate with one another and may be linked to each other using a network 702. The network 702 may include wireless and/or physical (e.g., hardwired) connections. Examples of networks include a telecommunications network of a service provider or carrier, Wide Area Network (WAN), a Local Area Network (LAN), a Wireless Local Area Network (WLAN), a cellular telecommunications network, a Wi-Fi network, a short range wireless network, a Wireless Metropolitan Area Network (WMAN), a Bluetooth® capable network, a fiber optic network, or a combination thereof. The network 702, generally, provides the components and devices access to the Internet and web-based applications.

The computing environment 700 comprises a computing device 704, which may be in the form of a server, as shown in the example of FIG. 7. Although illustrated as one component in FIG. 7, the present disclosure may utilize a plurality of local servers and/or remote servers in the computing environment 700. The computing device 704 may include components such as a processing unit, internal system memory, and a suitable system bus for coupling to various components, including electronic storage, memory, and the like, such as a data store, a database, and/or a database cluster. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced Industry Standard Architecture (EISA) bus, Video Electronics Standards Association (VESA) local bus, and Peripheral Component Interconnect (PCI) bus, also known as Mezzanine bus.

The computing device 704 may include or may have access to computer-readable media. Computer-readable media can be any available media that may be accessed by computing device 704, and includes volatile and nonvolatile media, as well as removable and non-removable media. By way of example, and not limitation, computer-readable media may include computer storage media and communication media. Computer storage media may include, without limitation, volatile and nonvolatile media, as well as removable and non-removable media, implemented in any method or technology for storage of information, such as computer-readable instructions, data structures, program modules, or other data. In this regard, computer storage media may include, but is not limited to, Random Access Memory (RAM), Read-Only Memory (ROM), Electrically Erasable Programmable Read-Only Memory (EEPROM), flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the computing device 704. Computer storage media does not comprise signals per se.

Communication media typically embodies computer-readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, radio frequency (RF), infrared, and other wireless media. Combinations of any of the above also may be included within the scope of computer-readable media.

In embodiments, the computing device 704 uses logical connections to communicate with one or more remote computers 706 within the computing environment 700. In embodiments where the network 702 includes a wireless network, the computing device 704 may employ a modem to establish communications with the Internet, the computing device 704 may connect to the Internet using Wi-Fi or wireless access points, or the server may use a wireless network adapter to access the Internet. The computing device 704 engages in two-way communication with any or all of the components and devices illustrated in FIG. 7, using the network 702. Accordingly, the computing device 704 may send data to and receive data from the remote computers 706 over the network 702.

Although illustrated as a single device, the remote computers 706 may include multiple computing devices. In an embodiment having a distributed network, the remote computers 706 may be located at one or more different geographic locations. In an embodiment where the remote computers 706 is a plurality of computing devices, each of the plurality of computing devices may be located across various locations such as buildings in a campus, medical and research facilities at a medical complex, offices or "branches" of a banking/credit entity, or may be mobile devices that are wearable or carried by personnel, or attached to vehicles or trackable items in a warehouse, for example.

In some embodiments, the remote computers 706 are physically located in a medical setting such as, for example, a laboratory, inpatient room, an outpatient room, a hospital, a medical vehicle, a veterinary environment, an ambulatory setting, a medical billing office, a financial or administrative office, hospital administration setting, an in-home medical care environment, and/or medical professionals' offices. By way of example, a medical professional may include physicians; medical specialists such as surgeons, radiologists, cardiologists, and oncologists; emergency medical technicians; physicians' assistants; nurse practitioners; nurses; nurses' aides; pharmacists; dieticians; microbiologists; laboratory experts; genetic counselors; researchers; veterinarians; students; and the like. In other embodiments, the remote computers 706 may be physically located in a non-medical setting, such as a packing and shipping facility or deployed within a fleet of delivery or courier vehicles.

Continuing, the computing environment 700 includes a data store 708. Although shown as a single component, the data store 708 may be implemented using multiple data stores that are communicatively coupled to one another, independent of the geographic or physical location of a memory device. Examples of data stores may store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. Examples of data stores may also store data in the form of electronic records, for example, electronic health records of patients, transaction records, billing records, task and workflow records, chronological event records, and the like.

Generally, the data store 708 includes physical memory that is configured to store information encoded in data. For example, the data store 708 may provide storage for computer-readable instructions, computer-executable instructions, data structures, data arrays, computer programs, applications, and other data that supports the functions and action to be undertaken using the computing environment 700 and components shown in the example of FIG. 7.

In a computing environment having distributed components that are communicatively coupled via the network 702, program modules may be located in local and/or remote computer storage media including, for example only, memory storage devices. Embodiments of the present disclosure may be described in the context of computer-executable instructions, such as program modules, being executed by a computing device. Program modules may include, but are not limited to, routines, programs, objects, components, and data structures that perform particular tasks or implement particular abstract data types. In embodiments, the computing device 704 may access, retrieve, communicate, receive, and update information stored in the data store 708, including program modules. Accordingly, the computing device 704 may execute, using a processor, computer instructions stored in the data store 708 in order to perform embodiments described herein.

Although internal components of the devices in FIG. 7, such as the computing device 704, are not illustrated, those of ordinary skill in the art will appreciate that internal components and their interconnection are present in the devices of FIG. 7. Accordingly, additional details concerning the internal construction device are not further disclosed herein.

Also, the present disclosure has been described in relation to particular embodiments, which are intended in all respects to be illustrative rather than restrictive. Thus the present disclosure is not limited to these embodiments, but variations and modifications may be made without departing from the scope of the present disclosure.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed is:

1. A computer-implemented method, comprising:

receiving, from an electronic database associated with an electronic health record system and with one or more hardware processors, a set of current data associated with a transport of a set of pharmaceutical drugs, the set of pharmaceutical drugs being identified in a listing associated with the transport and being associated with a corresponding one or more sets of features, wherein a set of features of the one or more sets of features includes pharmaceutical drug item information and transport information;

for each particular feature, of the one or more sets of features, generating via the one or more hardware processors impact scores based on a historical effect that the particular feature has had on a probability of diversion for each of the set of pharmaceutical drugs, wherein the generating of the impact scores for the one or more sets of features produces a set of impact scores;

identifying a set of impactful features, from the one or more sets of features, based on summing impact scores of the set of impact scores and based further on a predetermined impact score threshold;

executing a plurality of hardware based machine learning models via the one or more hardware processors to generate a diversion prediction for each machine learning model of the plurality of machine learning models, wherein:

a first machine learning model of the plurality of machine learning models is configured via the one or more hardware processors based on a set of diversion training data, a second machine learning model of the plurality of machine learning models is configured via the one or more hardware processors based on the set of diversion training data, the second machine learning model differing from the first machine learning model, and the diversion prediction for each machine learning model of the plurality of machine learning models corresponds to an effect of the set of impactful features on the probability of diversion for each of the set of pharmaceutical drugs;

determining that the first machine learning model is more accurate than the second machine learning model based on a comparison, via the one or more hardware processors, of the diversion prediction for each of the first machine learning model and the second machine learning model to a test data set associated with a set of historical-diversion data for each of the set of pharmaceutical drugs;

executing, via a computing device, the first machine learning model to determine a probability of diversion for the transport based on the set of impactful features and based further on the set of current data associated with the transport of the set of pharmaceutical drugs; and electronically writing, to a data structure associated with the electronic database and via the one or more hardware processors, a report data element comprising at least the probability of diversion for the transport.

2. The computer-implemented method of claim 1, wherein the probability of diversion for the transport represents a probability that a plurality of differing pharmaceutical drugs identified in the listing will be lost, stolen, or misplaced.

3. The computer-implemented method of claim 1, wherein the set of historical diversion data associated with each of the set of pharmaceutical drugs is automatically extracted from the electronic database associated with the electronic health record system by the computing device, and wherein the computing device is communicatively coupled with and configured to monitor an electronic health care record at the electronic health record system.

4. The computer-implemented method of claim 1, wherein for each feature of the set of features the historical effect that the feature has had on the probability of diversion is determined based on a percentage increase or decrease in the probability of diversion caused by the feature.

5. The computer-implemented method of claim 1, wherein:

the set of pharmaceutical drugs includes a first pharmaceutical drug identified in the listing and a second pharmaceutical drug identified in the listing, the one or more sets of features contains a first drug type for the first pharmaceutical drug and a second drug type for the second pharmaceutical drug, and executing the first machine learning model comprises applying, to the first machine learning model, content indicating (a) one or both of the first drug type and the first pharmaceutical drug but not (b) one or both of the second drug type and the second pharmaceutical drug.

6. The computer-implemented method of claim 1, wherein determining the probability of diversion for the transport comprises:

using the set of impactful features to generate the probability of diversion for each of the set of pharmaceutical drugs; and based on the probability of diversion for each of the set of pharmaceutical drugs, generating the probability of diversion for the transport.

7. The computer-implemented method of claim 1, wherein the probability of diversion for the transport is associated with a risk tier.

8. The computer-implemented method of claim 1, wherein a pharmaceutical drug order in the set of historical pharmaceutical drug diversion training data identifies a plurality of differing pharmaceutical drugs.

9. The computer-implemented method of claim 1, wherein the first machine learning model is determined to be more accurate based on executing the plurality of machine learning models using a same set of pharmaceutical drug diversion model input data that includes a drug order and multiple differing pharmaceutical drugs identified in the drug order.

10. The computer-implemented method of claim 1, further comprising accessing stored information indicating the plurality of machine learning models prior to executing the plurality of machine learning models.

11. The computer-implemented method of claim 10, wherein:

the first machine learning model is configured to generate a first diversion prediction based on at least one first attribute from a group comprising at least a first model algorithm, a first model learning method, and a first model restraint, and is further configured to generate the first diversion prediction based on a set of diversion training data; and the second machine learning model is configured to generate a second diversion prediction based on at least one second attribute from a group comprising at least a second model algorithm, a second model learning method, and a second model restraint, and is further configured to generate the second diversion prediction based on the set of diversion training data.

12. A computer system having one or more hardware processors configured to facilitate a plurality of operations, the operations comprising:

receiving, from an electronic database associated with an electronic health record system and with one or more hardware processors, a set of current data associated with a transport of a set of pharmaceutical drugs, the set of pharmaceutical drugs being identified in a listing associated with the transport and being associated with a corresponding one or more sets of features, wherein a set of features of the one or more sets of features includes pharmaceutical drug item information and transport information;

for each particular feature, of the one or more sets of features, generating via the one or more hardware processors impact scores based on a historical effect that the particular feature has had on a probability of diversion for each of the set of pharmaceutical drugs, wherein the generating of the impact scores for the one or more sets of features produces a set of impact scores;

identifying a set of impactful features, from the one or more sets of features, based on summing impact scores of the set of impact scores and based further on a predetermined impact score threshold;

executing a plurality of hardware based machine learning models via the one or more hardware processors to generate a diversion prediction for each machine learning model of the plurality of machine learning models, wherein:

a first machine learning model of the plurality of machine learning models is configured via the one or more hardware processors based on a set of diversion training data,

a second machine learning model of the plurality of machine learning models is configured via the one or more hardware processors based on the set of diversion training data, the second machine learning model differing from the first machine learning model, and the diversion prediction for each machine learning model of the plurality of machine learning models corresponds to an effect of the set of impactful features on the probability of diversion for each of the set of pharmaceutical drugs;

determining that the first machine learning model is more accurate than the second machine learning model based on a comparison, via the one or more hardware processors, of the diversion prediction for each of the first machine learning model and the second machine learning model to a test data set associated with a set of historical diversion data for each of the set of pharmaceutical drugs;

executing, via a computing device, the first machine learning model to determine a probability of diversion for the transport based on the set of impactful features and based further on the set of current data associated with the transport of the set of pharmaceutical drugs; and electronically writing, to a data structure associated with the electronic database and via the one or more hardware processors, a report data element comprising at least the probability of diversion for the transport.

13. The computer system of claim 12, wherein the predetermined impact score threshold is set via a user device input.

14. The computer system of claim 12, wherein the probability of diversion for the transport is associated with a risk tier.

15. The computer system of claim 14, wherein a first risk tier is associated with a first range of probability of diversion and a second risk tier is associated with a second range of probability of risk.

16. The computer system of claim 12, wherein the report data element comprises a table having at least three columns associated with the probability of diversion for the transport, information associated with the report data element and with an action, and a risk tier associated with the probability of diversion for the transport.

17. The computer system of claim 12, wherein the probability of diversion for the transport represents a probability that a plurality of differing pharmaceutical drugs identified in the listing will be lost, stolen, or misplaced.

18. The computer system of claim 12, wherein the set of historical diversion data associated with each of the set of pharmaceutical drugs is automatically extracted from the electronic database associated with the electronic health record system by the computing device, and wherein the computing device is communicatively coupled with and configured to monitor an electronic health care record at the electronic health record system.

19. The computer system of claim 12, wherein for each feature of the set of features the historical effect that the feature has had on the probability of diversion is determined based on a percentage increase or decrease in the probability of diversion caused by the feature.

20. One or more non-transitory media having instructions that, when executed by one or more hardware processors, cause the one or more hardware processors to facilitate a plurality of operations, the operations comprising:

receiving, from an electronic database associated with an electronic health record system and with one or more hardware processors, a set of current data associated with a transport of a set of pharmaceutical drugs, the set of pharmaceutical drugs being identified in a listing associated with the transport and being associated with a corresponding one or more sets of features, wherein a set of features of the one or more sets of features includes pharmaceutical drug item information and transport information;

for each particular feature, of the one or more sets of features, generating via the one or more hardware processors impact scores based on a historical effect that the particular feature has had on a probability of diversion for each of the set of pharmaceutical drugs wherein the generating of the impact scores for the one or more sets of features produces a set of impact scores;

identifying a set of impactful features, from the one or more sets of features, based on summing impact scores of the set of impact scores and based further on a predetermined impact score threshold;

executing a plurality of hardware based machine learning models via the one or more hardware processors to generate a diversion prediction for each machine learning model of the plurality of machine learning models, wherein:

a first machine learning model of the plurality of machine learning models is configured via the one or more hardware processors based on a set of diversion training data, a second machine learning model of the plurality of machine learning models is configured via the one or more hardware processors based on the set of diversion training data, the second machine learning model differing from the first machine learning model, and the diversion prediction for each machine learning model of the plurality of machine learning models corresponds to an effect of the set of impactful features on the probability of diversion for each of the set of pharmaceutical drugs;

determining that the first machine learning model is more accurate than the second machine learning model based on a comparison, via the one or more hardware processors, of the diversion prediction for each of the first machine learning model and the second machine learning model to a test data set associated with a set of historical diversion data for each of the set of pharmaceutical drugs;

executing, via a computing device, the first machine learning model to determine a probability of diversion for the transport based on the set of impactful features and based further on the set of current data associated with the transport of the set of pharmaceutical drugs; and electronically writing, to a data structure associated with the electronic database and via the one or more hardware processors, a report data element comprising at least the probability of diversion for the transport.

21. The one or more non-transitory media of claim 20, wherein executing the first machine learning model comprises applying, to the first machine learning model, content indicating (a) one or both of a first drug type contained in the listing and/or a first pharmaceutical drug contained in the listing but not (b) one or both of a second drug type contained in the listing and/or a second pharmaceutical drug contained in the listing.

22. The one or more non-transitory media of claim 20, wherein the set of historical diversion data associated with each of the set of pharmaceutical drugs is automatically extracted from the electronic database associated with the electronic health record system by the computing device, and wherein the computing device is communicatively coupled with and configured to monitor an electronic health care record at the electronic health record system.

23. The one or more non-transitory media of claim 20, wherein the probability of diversion for the transport represents a probability that a plurality of differing pharmaceutical drugs identified in the listing will be lost, stolen, or misplaced.

24. The one or more non-transitory media of claim 23, wherein for each feature of the set of features the historical effect that the feature has had on the probability of diversion is determined based on a percentage increase or decrease in the probability of diversion caused by the feature.

* * * * *